US011969526B2

(12) United States Patent
Appel et al.

(10) Patent No.: US 11,969,526 B2
(45) Date of Patent: Apr. 30, 2024

(54) ADHESION PREVENTION WITH SHEAR-THINNING POLYMERIC HYDROGELS

(71) Applicant: The Board of Trustees of the Leland Stanford Junior University, Palo Alto, CA (US)

(72) Inventors: Eric Andrew Appel, Stanford, CA (US); Y. Joseph Woo, Atherton, CA (US); Lyndsay Stapleton, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 399 days.

(21) Appl. No.: 15/943,358

(22) Filed: Apr. 2, 2018

(65) Prior Publication Data
US 2018/0280586 A1  Oct. 4, 2018

Related U.S. Application Data

(60) Provisional application No. 62/480,636, filed on Apr. 3, 2017.

(51) Int. Cl.
*A61L 31/04*  (2006.01)
*A61L 31/06*  (2006.01)
*A61L 31/14*  (2006.01)

(52) U.S. Cl.
CPC ........... *A61L 31/041* (2013.01); *A61L 31/042* (2013.01); *A61L 31/06* (2013.01); *A61L 31/145* (2013.01); *A61L 2300/424* (2013.01); *A61L 2400/12* (2013.01)

(58) Field of Classification Search
CPC ...... A61L 31/041; A61L 31/042; A61L 31/06; A61L 31/145; A61L 2400/12; A61L 2300/424
See application file for complete search history.

(56) References Cited

U.S. PATENT DOCUMENTS

| | | | |
|---|---|---|---|
| 4,192,727 A | 3/1980 | Ward | |
| 5,143,724 A | 9/1992 | Leshchiner et al. | |
| 5,410,016 A | 4/1995 | Hubbell et al. | |
| 5,480,436 A | 1/1996 | Bakker et al. | |
| 5,785,993 A | 7/1998 | Baker et al. | |
| 5,888,988 A | 3/1999 | Elson | |
| 6,150,581 A | 11/2000 | Jiang et al. | |
| 6,673,093 B1 | 1/2004 | Sawhney | |
| 6,818,018 B1 | 11/2004 | Sawhney | |
| 7,125,860 B1 | 10/2006 | Renier et al. | |
| 7,347,850 B2 | 3/2008 | Sawhney | |
| 8,455,001 B2 | 6/2013 | Ito et al. | |
| 8,709,450 B2 | 4/2014 | Kaneko et al. | |
| 8,728,524 B2 | 5/2014 | Bellini et al. | |
| 8,748,409 B2 | 6/2014 | Kaneko et al. | |
| 8,778,326 B2 | 7/2014 | Lu et al. | |
| 8,859,523 B2 | 10/2014 | Prestwich et al. | |
| 8,916,143 B2 | 12/2014 | Putnam et al. | |
| 9,089,730 B2 | 7/2015 | Shalev et al. | |
| 9,289,279 B2 | 3/2016 | Wilson et al. | |
| 2002/0042473 A1* | 4/2002 | Trollsas | A61L 31/16 525/54.1 |
| 2003/0180251 A1 | 9/2003 | Friedrich et al. | |
| 2004/0023842 A1 | 2/2004 | Pathak et al. | |
| 2005/0271727 A1 | 12/2005 | Yao | |
| 2006/0177481 A1 | 8/2006 | Sawhney | |
| 2007/0001156 A1 | 1/2007 | Toreki | |
| 2008/0069857 A1 | 3/2008 | Yeo et al. | |
| 2008/0107703 A1 | 5/2008 | Tabata et al. | |
| 2009/0294049 A1 | 12/2009 | Udipi et al. | |
| 2010/0285113 A1 | 11/2010 | Shoichet et al. | |
| 2010/0291055 A1 | 11/2010 | Athanasiadis et al. | |
| 2011/0178184 A1 | 7/2011 | Kaneko et al. | |
| 2012/0298777 A1* | 11/2012 | Holladay | A61L 26/008 239/328 |
| 2015/0202299 A1 | 7/2015 | Burdick et al. | |
| 2016/0030789 A1 | 2/2016 | Cordani | |
| 2016/0228601 A1 | 8/2016 | He et al. | |
| 2016/0287745 A1 | 10/2016 | Grinstaff et al. | |
| 2017/0196818 A1 | 7/2017 | Shin et al. | |
| 2017/0319506 A1 | 11/2017 | Appel et al. | |

(Continued)

FOREIGN PATENT DOCUMENTS

EP   2511336 B1   10/2012
KR   20060011503 A   2/2006

(Continued)

OTHER PUBLICATIONS

Prestwich, "Engineering a clinically-useful matrix for cell therapy", Organogenesis 4:1, pp. 42-47, 2008.*

(Continued)

*Primary Examiner* — Melissa S Mercier
(74) *Attorney, Agent, or Firm* — Kilpatrick Townsend & Stockton LLP

(57) ABSTRACT

A tissue adhesion prevention hydrogel is provided and engineered with essential features for maintaining separation between tissues and organs in any part of the body, thus preventing adhesion formation, are their shear-thinning, viscoelasticity, and rapid self-healing. A method of using the tissue adhesion prevention hydrogel for tissue adhesion prevention is also provided. A method of interposing the tissue adhesion prevention in between tissue layers for tissue adhesion prevention is further provided.

21 Claims, 15 Drawing Sheets

(56) References Cited

U.S. PATENT DOCUMENTS

2017/0362380 A1   12/2017   Christman et al.
2018/0086896 A1   3/2018    Appel et al.

FOREIGN PATENT DOCUMENTS

| KR | 20170110882 A | 10/2017 | |
|---|---|---|---|
| WO | WO93/17669 A1 | 9/1993 | |
| WO | WO03/084481 A2 | 10/2003 | |
| WO | WO2005/110377 A1 | 11/2005 | |
| WO | WO2013/076305 A1 | 5/2013 | |
| WO | WO2013/124654 A1 | 8/2013 | |
| WO | WO2013124654 | 8/2013 | |
| WO | WO2014/116187 A1 | 7/2014 | |
| WO | WO2014/125418 A1 | 8/2014 | |
| WO | WO2015/172073 A1 | 11/2015 | |
| WO | WO2016/049360 A1 | 3/2016 | |
| WO | WO2016049360 | 3/2016 | |
| WO | WO-2016049360 A1 * | 3/2016 | ............. A61K 47/30 |

OTHER PUBLICATIONS

Grosskopf et al.; Injectable supramolecular polymer-nanoparticle hydrogels enhance human mesenchhymal stem cell delivery; Bioengineering & Translational Medicine, vol. e10147; pp. 1-11; Oct. 12, 2019.
Appel et al.; U.S. Appl. No. 16/709,832 entitled "Biometric, moldable, self-assembled cellulose silica-based trimeric hydrogels and their use as viscosity modifying carriers in industrial applications," filed Dec. 10, 2019.
Bremer et al.; Laboratory scale clean-in-place (CIP) studies on the effectiveness of different caustic and acid wash steps on the removal of dairy biofilms; Intl. J. of Food Microb.; 106(3); pp. 254-262; Feb. 15, 2006.
Drevelle et al.; Thermal and fire behaviour of ammonium polyphosphate/acrylic coated cotton/PESFR fabric; Polymer Degradation and Stability; 88(1); pp. 130-137; Apr. 1, 2005.
Ehrbar et al.; Drug-sensing hydrogels for the inducible release of biopharmaceuticals; Nature materials; 7(10); pp. 800-804; Oct. 2008.
Gesan-Guiziou et al.; Nanofiltration for the recovery of caustic cleaning-in-place solutions: robustness towards large variations of composition; Journal of Dairy Research; 69(4); pp. 633-643; Nov. 2002.
Gu et al.; Study on preparation and fire-retardant mechanism analysis of intumescent flame-retardant coatings; Surface and coatings tech.; 201(18); pp. 7835-7841; Jun. 25, 2007.
Hales et al.; Ice fraction measurement of ice slurries through electromagnetic attenuation; Intl. J. of Refrig.; 47; pp. 98-104; Nov. 1, 2014.
Kapsabelis et al.; Adsorption of ethyl (hydroxyethyl) cellulose onto silica particles: the role of surface chemistry and temperature; J. of colloid and interface sci.; 228(2); pp. 297-305; Aug. 15, 2000.
Moody et al.; Monitoring perfluorinated surfactants in biota and surface water samples following an accidental release of firefighting foam into Etobicoke Creek; Environ. Sci. and Tech.; 36(4); pp. 545-551; Feb. 15, 2002.
Moody et al.; Occurrence and persistence of perfluorooctanesulfonate and other perfluorinated surfactants in groundwater at a fire-training area at Wurtsmith Air Force Base, Michigan, USA; J. Environ. Mon.; 5(2); pp. 341-345; Mar. 10, 2003.
Moody et al.; Perfluorinated surfactants and the environmental implications of their use in fire-fighting foams; Environ. Scl. and Technol.; 34(18); pp. 3864-3870; Sep. 15, 2000.
Schroeder, D.; Can fire suppressant gels protect log decks. A case study to test the concept; Wildland Fire Operations Research Group; Vancouver; (year of pub. sufficiently earlier than effective US filing date and any foreign priority date) 2005.
Schroeder, D.; Can fire suppressant gels protect log decks? Part III—Two case studies to test gel effectiveness against radiant and convective heat transfer; Vancouver; (year of pub. sufficiently earlier than effective US filing date and any foreign priority date) 2006.
Schroeder, D.; Effectiveness of forest fuel management: a crown fire case study in the Northwest Territories, Canada; Forest Eng. Res. Inst. of Canada, Vancouver; (year of pub. sufficiently earlier than effective US filing date and any foreign priority date) 2006.
Tamesue et al.; Linear versus dendritic molecular binders for hydrogel network formation with clay nanosheets: studies with ABA triblock copolyethers carrying guanidinium ion pendants; J. Am. Chem. Soc.; 135 (41); pp. 15650-15655; Oct. 3, 2013.
Yamaguchi et al.; Self-assembly of gels through molecular recognition of cyclodextrins: Shape selectivity for linear and cyclic guest molecules; Macromolecules; 44(8); pp. 2395-2399; Mar. 25, 2011.
Xu et al.; Genetically engineered block copolymers: influence of the length and structure of the coiled-coil blocks on hydrogel self-assembly; Pharm. Res.; 25(3); pp. 674-682; Mar. 1, 2008.
Bao et al.; Swelling behaviors of organic/inorganic composites based on various cellulose derivatives and inorganic particles; Carbohydrate Polymers; 88(2); pp. 589-595; Apr. 2012.
Artivashist et al.; Hydrogels: Smart materials for drug delivery; Oriental Journal of Chemistry; 29(3); pp. 861-870; Nov. 5, 2013.
Appel et al.; Activation energies control the macroscopic properties of physically cross-linked materials; Angew. Chem. Ind. Ed .; 53; 7 pgs.; Sep. 15, 2014.
Appel et al.; Formation of single-chain polymer nanoparticles in water through host-guest interactions; Angew. Chem. Int. Ed.; 51; pp. 4185-4189; Apr. 23, 2012.
Appel et al.; Gluing Gels: A nanoparticle solution; Nature Materials; 13(3); pp. 231-232; Mar. 2014.
Appel et al.; Sustained release of proteins from high water content supramolecular polymer hydrogels; Biomaterials; 33(18); pp. 4646-4652; Jun. 1, 2012.
Appel et al.; The control of cargo release from physically cross-linked hydrogels by crosslink dynamics; Biomaterials; 35(37); pp. 9897-9903; Dec. 1, 2014.
Evans et al.; Investigation into the transportation and melting of thick ice slurries in pipes; Intl. Journal of Refrig.; 31(1); pp. 145-151; Jan. 1, 2008.
Gimenez et al.; Long-term forest fire retardants: a review of quality, effectiveness, application and environmental considerations; Intl. J. of Wildland Fire; 13(1); pp. 1-15; Apr. 27, 2004.
Harada et al.; Macroscopic self-assembly through molecular recognition; Nature Chem.; 3(1); pp. 34-37; Jan. 2011.
Hu et al.; Detection of poly- and perfluoroalkyl substances (PFASs) in U.S. drinking water linked to industrial sites, military fire training areas, and wastewater treatment plants; Env. Sci, and Tech. Letters; 3(10); pp. 344-350; Aug. 9, 2016.
Krishna et al.; Protein- and oeptide-modified synthetic polymeric biomaterials; Peptide Science: Original Res. On Biomolecules; 94(1); pp. 32-48; Jan. 20, 2010.
Maupin et al.; Estimated use of water in the United States in 2010; USGS Survey (No. 1405); 64 pgs.; (year of pub. sufficiently earlier than effective US filing date and any foreign priority date) 2014.
Merin et al.; Cleaning-in-place in the dairy industry: criteria for reuse of caustic (NaOH) solutions; Le Lait; 82(3); pp. 357-366; May 1, 2002.
Mulyasasmita et al.; Moleculr-level engineering of protein physical hydrogels for predictive sol-gel phase behavior; Biomacromolecules; 12(10); pp. 3406-3411; Sep. 2, 2011.
Nakahata et al.; Redox-responsive self-healing materials formed from host-guest polymers; Nature Comm.; 2(511); pp. 1-6; Oct. 25, 2011.
Quarini, J.; Ice-pigging to reduce and remove fouling and to achieve clean-in-place; Applied thermal Eng.; 22(7); pp. 747-753; May 1, 2002.
Quarini et al.; Investigation and development of an innovative pigging technique for the water-supply industry; Proc. Inst. Mech. Eng., Part E: J. Proc. Mech. Eng.; 224(2); pp. 79-89; May 1, 2010.
Rodell et al.; Shear-thinning supramolecular hydrogels with secondary autonomous covalent crosslinking to modulate viscoelastic properties in vivo; Adv. Functional Mat.; 25(4); pp. 636-644; Jan. 28, 2015.

(56) References Cited

OTHER PUBLICATIONS

Rose et al.; Nanoparticle solutions as adhesives for gels and biological tissues; Nature; 505(7483); pp. 382-385; Jan. 16, 2014.
Rowland et al.; Dynamically crosslinked materials via recognition of amino acids by cucurbit [8] uril; J. Mat. Chem. B; 1(23); pp. 2904-2910; Apr. 30, 2013.
Salem et al.; Porous polymer and cell composites that self-assemble in situ; Advanced Materials; 15(3); pp. 210-213; Feb. 5, 2003.
Yamaguchi et al.; Photoswitchable gel assembly based on molecular recognition; Nature Comm.; 3(603); pp. 1-5; Jan. 3, 2012.
Xu et al.; Reversible hydrogels from self-assembling genetically engineered protein block copolymers; Biomacromolecules; 6(3); pp. 1739-1749; May 9, 2005.
Appel et al.; Expoiting electrostatic interactions in polymer-nanoparticle hydrogels; ACS Macro letters; 4(8); pp. 848-852; Jul. 27, 2015.
Appel et al.; Self-assembled hydrogels utilizing polymer-nanoparticle interactions; Nature Communications; 6; pp. 6295; doi: 10:1038/ncomms7295; 19 pages; (Author Manuscript); Feb. 19, 2015.
Appel et al.; Supramolecular cross-linked metworks via host-guest complexation with cucurbit[8] uril; Journal of the American Chemical Society; 132(40); pp. 14251-14260; Sep. 16, 2010.
Appel et al.; Supramolecular polymeric hydrogels; Chemical Society Reviews; 41(18); pp. 6195-6214; Sep. 2012.
Chen et al.; Injectable thermosensitive hydrogel containing hyaluronic acid and chitosan as barrier for prevention of postoperative peritoneal adhesion; Carbohydr. Polm.; 173; pp. 721-731; doi:10.1016/j.carbpol.2017.06.019; Oct. 2017.
Fu et al.; Biodegradable and thermosensitive monomethoxy poly-(ethylene glycol)- poly(lactic acid) hydrogel as a barrier for prevention of post-operative abdominal adhesion; journal of Biomedical Nanotechnology; 10(3); pp. 427-435; Mar. 2014.
Hoare et al.; Prevention of peritoneal adhesions using polymeric rheological blends; Acta Biomaterialia; 10(3); pp. 1187-1193; 16 pages; (Author Manuscript); Mar. 2014.
Karacam et al.; Prevention of pleural adhesions using a membrane containing polyethylene glycol in rats; International Journal of Medical Sciences; 8(5); pp. 380-386; (year of pub. sufficiently earlier than effective US filing date and any foreign priority date); 2011.
Krielen et al.; In-hospital costs of an admission for adhesive small bowel obstruction; World Journal of Emergency Surgery; 11(1); p. 49; DOI 10.1186/s13017-016-0109-y; 8 pages; Dec. 2016.
Lu et al.; Injectable shear-thinning hydrogels engineered with a self-assembled dock-and-lock mechanism; Biomaterials; 33(7); pp. 2145-2153; Mar. 2012.
Osada et al.; The effect of cross-linked hyaluronate hydrogel on the reduction of post-surgical adhesion reformation in rabbits; Journal of International Medical Research; 5; pp. 233-241; Sep. 1999.
Parisi-Amon et al.; Protein-engineered injectable hydrogel to improve retention of transplanted adipose-derived stem cells; Advanced Healthcare Materials; 2(3); pp. 428-432; 10 pages; (Author Manuscript); Mar. 2013.
Petka et al.; Reversible hydrogels from self-assembling artifical proteins; Science; 281(5375); pp. 389-392; Jul. 17, 1998.
Pritchard et al.; An injectable thiol-acrylate poly(ethylene glycol) hydrogel for sustained release of methylprenisolone sodium succinate; Biomaterials; 32(2); pp. 587-597; 30 pages; (Author Manuscript); Jan. 2011.
Rodell et al.; Rational design of network properties in guest-host assembled and shear-thinning hyaluronic acid hydrogels; Biomacromolecules; 14(11); pp. 4125-4134; 20 pages; (Author Manuscript); Oct. 14, 2013.
Shi et al.; Polymeric hydrogels for post-operative adhesion prevention: a review; Materials Express; 7(6); pp. 417-438; Dec. 2017.
Song et al.; Peritoneal adhesion prevention with a biogradable and injectable N, O-carboxymethyl chitosan-aldehyde hyaluronic acid hydrogel in a rat repeated injury model; Scientific Reports; 6; doi: 10.1038/srep37600; 13 pages; Nov. 21, 2016.
Stapleton et al.; A novel, shear-assembling shear-thinning polymer-nanoparticle hydrogel diminishes post-operative thoracic adhesion in a podent model of ischemic cardiomyopathy; Circulation; 136(1); Abstract 21311; 6 pages; (Abstract Only); Jun. 9, 2018.
Wang et al.; High-water-content mouldable hydrogels by mixing clay and a dendritic molecular binder; Natue 463(7279); pp. 339-343; Jan. 2010.
Webber et al.; Supramolecular biomaterials; Nature Materials; 15(1); pp. 13-26; Jan. 2016.
Wong Po Foo et al.; Two-component protein-engineered physical hydrogels for cell encapsulation; Proceedings of the National Academy of Sciences; 106(52); pp. 22067-22072; doi: 10.1073/pnas.0904851106; 6 pages; Dec. 29, 2009.
Yeo et al.; Polymers in the prevention of peritoneal adhesions; European Journal of Pharaceutics and Biopharmaceutics; 68(1); pp. 57-66; 16 pages; (Author Manuscript); Jan. 2008.
Yu et al.; Comparative studies of thermogels in preventing post-operative adhesions and corresponding mechanisms; Biomater. Sci.; 2(8); pp. 1100-1109; doi: 10.1039/C4M00029C; retrived from the internet (http://pubs.rsc.org/-/content/articlehtml/2014/bm/c4bm00029c); 30 pages; (year of pub. sufficiently earlier than effective US filing date and any foreign priority date) 2014.
Zhang et al.; Biodegradable and thermoreversible PCLA-PEG-PCLA hydrogel as a barrier for prevention of post-operative adhesion; Biomaterials; 32(21); pp. 4725-4736; Jul. 2011.
Appel et al.; Ultrahigh-water-content supramolecular hydrogels exhibiting multistimuli responsiveness; J. Am. Chem. Soc.; 134(28); pp. 11767-11773; Jul. 18, 2012.
Bang et al.; Injectable pullulan hydrogel for the prevention of postoperative tissue adhesion; International Journal of Biological Macromolecules; 87; pp. 155-162; Jun. 2016.
Ishiyama et al.; The prevention of peritendinous adhesions by phospholipid polymer hydrogel formed in situ by spontaneous intermolecular interactions; Biomaterials; 31(14); pp. 4009-4016; May 2010.
Okabayashi et al.; Adhesions after abdominal surgery: a systematic review of the incidence, distribution and severity; Surgery Today; 44(3); pp. 405-420; Mar. 1, 2014.
Park et al.; In situ supramolecular assembly and modular modification of hyaluronic acid hydrogels for 3D cellular engineering; ACS Nano; 6(4); pp. 2960-2968; Mar. 15, 2012.
Shen et al.; Tuning the erosion rate of artifical protein hydrogels through control of network topology; Nature Materials; 5(2); pp. 153-158; Feb. 2006.
Yang et al.; A postoperative anti-adhesion barrier based on photoinduced imine-crosslinking hydrogel with tissue-adhesive ability; Acta Biomaterialia; 62; pp. 199-209; Oct. 15, 2017.
Zhu et al.; Metal and light free "click" hydrogels for prevention of post-operative peritoneal adhesions; Polymer Chemistry; 5(6); pp. 2018-2026; (year of pub. sufficiently earlier than effective US filing date and any foreign priority date) 2014.
Bourges et al.; Synthesis and General Properties of Silated-Hydroxypropyl Methylcellulose in Prospect of Biomedical Use; Advances in Colloid and Interface Science; 99 (3), pp. 215-228; Dec. 2, 2002.
Patterson et al.; In situ characterization of the degradation of PLGA microspheres in hyaluronic acid hydrogels by optical coherence tomography; IEEE Transactions on Medical Imaging; vol. 28; pp. 74-81; Jan. 2009.
Wang et al.; PLGA-chitosan/PLGA-alginate nanoparticle blends as biodegradable colloidal gels for seeding human umbilical cord mesenchymal stem cells; Journal of Bionedical Research, Part A; 96(3); pp. 520-527; (Author Manuscript) Mar. 2011.
Appeal et al.; U.S. Appl. No. 16/590,189 entitled "Adhesion prevention with shear-thinning polymeric hydrogels," filed Oct. 1, 2019.
Richards; Cancer immunotherapy gets assist from micro-scale engineering; 7 pages; retrieved from the internet (https://www.fredhutch.org/en/news/center-news/2019/12/stephan-thin-film-stent-immunotherapy.html) on Nov. 11, 2021.
Agmon et al.; U.S. Appl. No. 17/281,014 entitled "Injectable hydrogels for controlled release of immunomodulatory compounds," filed Mar. 29, 2021.

(56) References Cited

OTHER PUBLICATIONS

Adusumilli et al.; Regional delivery of mesothelin-targeted car t cell therapy generates potent and long lasting cd4-dependent tumor immunity; Science Translational Medicine; 6(261); pp. 261ra151-261ra151; 31 pages; (Author Manuscript); Nov. 2014.

Anthony et al.; Physical networks from entropy-driven non-covalent interactions; Nature Communications; 12(1); pp. 1-9; Feb. 2021.

Anthony et al.; Scalable manufacturing of biomimetic moldable hydrogels for industrial applications; Porceedings National Academy Sciences; 113(50); pp. 14255-14260; Dec. 2016.

Cheung et al.; Scaffolds that mimic antigen-presenting cells enable ex vivo expansion of primary t cells; Nature Biotechnology; 36(2); 160-169; 29 pages; (Author Manuscript); Feb. 2018.

Conlon et al.; Redistribution, hyperproliferation, activation of natural killer cells and CD8 T cells, and cytokine production during first-in-human clinical trail of recombinant human interleukin-15 in patients with cancer; Journal of Clinical Oncology; 33(1); pp. 74-82; Jan. 2015.

Hall et al.; Engineered luciferase reporter from a deep sea shrimp utilizing a novel imidazopyrazinone substrate; ACS Chemical Bilogy; 7(11); pp. 1848-1857; Nov. 2012.

Hughes et al.; Transfer of a tor gene derived from a patient with marked antitumor response conveys highly active t-cell effector functions; Human Gene Therapy; 16(4); pp. 457-472; 25 pages; (Author Manuscript); Apr. 2005.

Labanieh et al.; Programming car-t-cells to kill cancer; Nature Biomedical Engineering; 2(6); pp. 377-391; (year of pub. sufficiently earlier than effective US filing date and any foreign priority date) 2018.

Long et al.; 4-1BB costimulation ameliorates t cell exhaustion induced by tonic signaling of chimeric antigen receptors; Nature Medicine; 21(6); pp. 581-590; 27 pages; (Auhtor Manuscript); Jun. 2015.

Lopez Hernandez et al.; A quantitative description for designing the extrudability of shear-thinning physical hydrogels; Macromolecular Bioscience; 21(2); 2000295; 10 pages; Feb. 2021.

Lotze et al.; Clinical effects and toxicity of interleukin-2 in patients with cancer; Cancer; 58(12); pp. 2764-2772; Dec. 1986.

Miller et al.; A first-in-human phase 1 study of subcutaneous outpatient human 1L15 (rhIL15) in adult with advanced solid tumors; Clinical Cancer Research; 24(7); pp. 1525-1535; Apr. 2018.

Ring et al.; Mechanistic and structural insight into the functional dichotomy between il-2 and il-15; Nature Immunology: 13(12); pp. 1187-1195; 26 pages; (Author Manuscript): Dec. 2012.

Shaner et al.; A bright monomeric green fluorescent protein derived from branchiostoma lanceolatum; Nature Methods; 10(5); pp. 407-409; 18 pages; (Author Manuscript); May 2013.

Stephan et al.; Bipolymer implants enhance the efficacy of adoptive t-cell therapy; Nature Biotechnology; 33(1); pp. 97-101; 18 pages; (Author Manuscript); Janaury 2015.

Waldmann et al.; Safety (toxicity), pharmacokinetics, immunogenicity, and impact on elements of the normal immune system of recombinant human il-15 in rhesus macaques; Blood, The Journal American Society Hermatology; 117(18); pp. 4787-4795; May 2011.

Liu, et al., Reduced postoperative intra-abdominal adhesions using Carbylan-SX, a semisynthetic glycosaminoglycan hydrogel, Fertility and Sterility, Apr. 2007, vol. 87, No. 4, American Society for Reproductive Medicine, Published by Elsevier Inc.

\* cited by examiner

Infarct induction with suture

Administration of Physical Hydrogel

ADHESION PREVENTION WITH SHEAR-THINNING POLYMERIC HYDROGELS

CROSS-REFERENCE TO RELATED APPLICATIONS

This application claims priority from U.S. Provisional Patent Application 62/480,636 filed Apr. 3, 2017, which is incorporated herein by reference.

FIELD OF THE INVENTION

This invention relates to shear-thinning polymeric hydrogels to prevent adhesions that abnormally form between internal organs and tissues following surgery, infections, and other types of bodily insult.

BACKGROUND OF THE INVENTION

Adhesions are fibrous bands of scar tissue that abnormally form between internal organs and tissues following surgery, infections, and other types of bodily insult. The incidence of adhesions commonly occurs following abdominal, gynecological, thoracic, and orthopedic surgery, resulting in severe pain, bowel obstruction, infertility and often require re-operation, depending on the type of surgery. Abdominal adhesions are widely studied, where the incidence of adhesions following surgery is estimated to be as high as 93%. Although a vast number of therapeutic agents (e.g., anti-inflammatory drugs), physical barriers, polymers for controlled drug release, and polymeric rheological blends have been studied in the prevention of post-operative adhesions, the prevention of these adhesions remains a significant challenge.

Pericardial adhesions, although not widely studied, pose a serious risk of complications to patients—especially to those needing secondary or tertiary operations due to increased operation times, hemorrhage, morbidity, and mortality. Indeed, surgeons must often spend upwards of 4 hours cutting through adhesions before the necessary surgery can begin. Moreover, adhesions increase the risk of cardiac injury during reoperation and reentry. Post-operative adhesions affect millions of people around the world and result in a significant healthcare expenses to combat the complications associated with their formation.

Current solutions available for commercial use are typically polymer films based on polysaccharides and/or synthetic polymers (both resorbable and non-resorbable varieties), which serve as a physical barrier between scarring tissue and surrounding organs. Other technologies that have been tested are based on sprayable pre-polymer solutions that polymerize into polymeric hydrogel films in situ, or which are simple polymer solutions. For polymer solutions comprising, for example, chitosan, hyaluronic acid (HA) and/or carboxymethylcellulose (CMC), the residence time at the injured tissues is too short. For resorbable solid membranes including HA-CMC (Seprafilm, Genzyme, Cambridge, MA) and polylactide, it is difficult to completely cover the affected tissues during application, which is particularly problematic in areas of the body with many surfaces that may form adhesions, such as in the abdomen. Despite the overwhelming need, current adhesion barrier technologies have not been widely adopted due to their inefficacy to fully limit adhesions, rapid degradation time, and difficulty handling during surgery. The present invention advances the art and introduces a different adhesion prevention technology.

SUMMARY OF THE INVENTION

A tissue adhesion prevention hydrogel is provided and engineered with essential features for maintaining separation between tissues and organs, thus preventing adhesion formation, are their shear-thinning, viscoelasticity, and rapid self-healing. The tissue adhesion prevention hydrogel comprises a shear-thinning and viscoelastic supramolecular hydrogel. In one embodiment, the shear-thinning supramolecular hydrogel comprises hydroxypropylmethylcellulose (HPMC). In another embodiment, the shear-thinning supramolecular hydrogel comprises poly(ethyleneglycol)-block-poly(lacticacid) (PEG-PLA) nanoparticles. Specifically, the physical characteristics of the shear-thinning supramolecular hydrogel, which provide the adhesion prevention are:
- a storage modulus (G') of 10-1000 Pa observed at a frequency of 10 rad/s and at a strain within the linear viscoelastic regime of the material using an oscillatory shear test in a parallel plate rheometer;
- a yield stress of 1-1000 Pa observed using a stress ramp in a parallel plate rheometer;
- a linear viscoelasticity maintained at strains up to at least 0.5% observed in an oscillatory strain amplitude sweep observed at a frequency of 10 rad/s in a parallel plate rheometer; and
- a Tan Delta, defined as the ratio of the loss modulus over the storage modulus, G"/G', less than 1 when observed in an oscillatory shear test at a frequency of 10 rad/s and a strain within the linear viscoelastic regime of the material using a parallel plate rheometer.

The present invention also provides a method of using the tissue adhesion prevention hydrogel for tissue adhesion prevention. The present invention further provides a method of interposing the tissue adhesion prevention in between tissue layers for tissue adhesion prevention.

BRIEF DESCRIPTION OF THE DRAWINGS

FIG. 5A shows a schematic illustration of induced myocardial infarction in the heart of a rat, whereby the left anterior descending artery (LAD) is sutured to prevent blood flow to the myocardium, leading to local myocardial infarction. Preliminary studies assessing formation of pericardial adhesions with no treatment or application of either standard-of-care treatments or our anti-adhesion shear-thinning and self-healing hydrogel.

DETAILED DESCRIPTION

Figure 1:
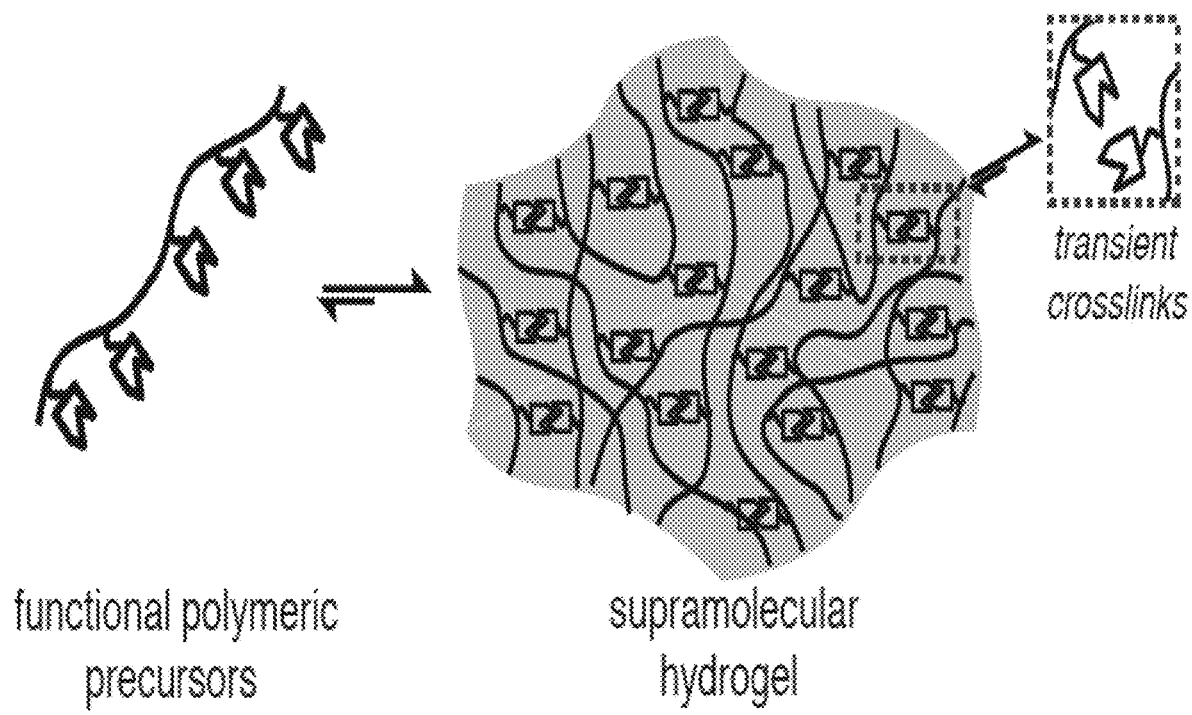
FIG. 1 shows according to an exemplary embodiment of the invention a schematic representation of supramolecular hydrogel systems utilizing functional polymer precursors. These hydrogel materials are shear-thinning and self-healing on account of their transient, non-covalent cross-linking between polymer chains.
Figure 2:
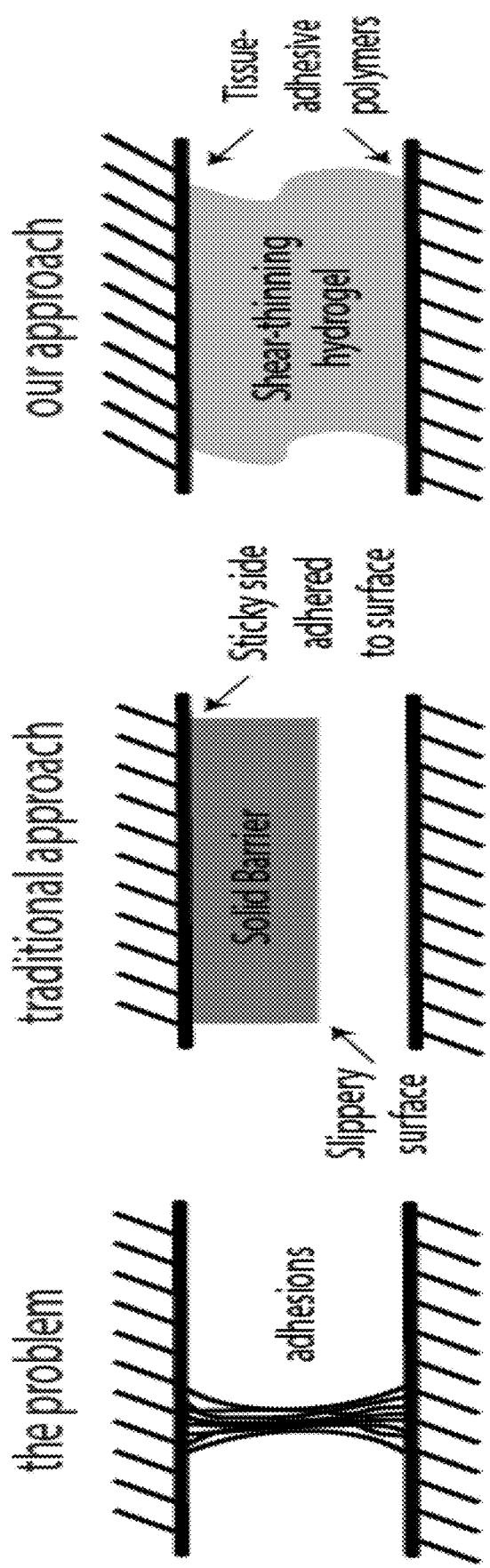
FIG. 2 shows according to an exemplary embodiment of the invention shear-thinning, self-healing, and viscoelastic materials for adhesion prevention. Schematic representation of an adhesion forming between two tissue surfaces (left), traditional solid adhesion barriers (middle) and the approach of the present invention for anti-adhesion technology (right) based on shear-thinning, self-healing polymeric hydrogels. Traditional solid adhesion barriers can often become dislodged and/or degrade too quickly, preventing them from functioning correctly. We have developed a platform of dynamically cross-linked supramolecular hydrogels that include hydroxypropylmethylcellulose (HPMC, allowing these materials to adhere well to tissues in the body. These materials can be sprayed, allowing for straightforward application following surgery, while their viscoelastic mechanical properties maintain lubricity between tissues, preventing adhesions.

Shear-thinning and self-healing biomaterials provide an innovative solution to the adhesion prevention problem. Traditional hydrogel systems utilize covalent crosslinks between polymer chains and are well-suited for a range of applications on account of their high-water content and highly tunable mechanical properties, yet the irreversibility of their crosslinks generally makes them brittle. Some of these materials can be prepared in situ by polymerization of a pre-polymer solution that can be applied by spraying. Yet, while the application of these materials can be relatively easy, the in situ polymerization has many potential side-effects, including in some circumstances cross-linking of the native tissues leading to greater adhesion formation. Moreover, polymer solutions, while simple to apply, are only mildly effective at preventing adhesions. In contrast, however, the specific, tunable, and reversible nature, supramolecular hydrogels that are both shear-thinning and rapidly self-healing offers many benefits over traditional hydrogels. Utilizing non-covalent interactions (FIG. 1), supramolecular hydrogels exhibiting viscous flow under shear stress (shear-thinning) and rapid recovery when the applied stress is relaxed (self-healing) can be created. Instead of providing a solid barrier between tissues and organs, the supramolecular hydrogel creates a shear-thinning and viscoelastic barrier between the two surfaces similar to the body's natural state (FIG. 2).

Polymer-nanoparticle (PNP) interactions are an assembly motif for tunable, shear-thinning, and self-healing materials without the need for complex synthetic approaches or specialized small-molecule binding partners. The inventors herein propose the use of hydrogels utilizing PNP interactions between hydrophobically modified cellulose derivatives and NPs comprising poly(ethylene glycol)-block-poly (lactic acid) (PEG-PLA). These hydrogels can be used as a straightforward-to-apply, shear-thinning and viscoelastic material to prevent adhesions in any part of the body following any type of surgery or bodily insult.

Figure 3A:
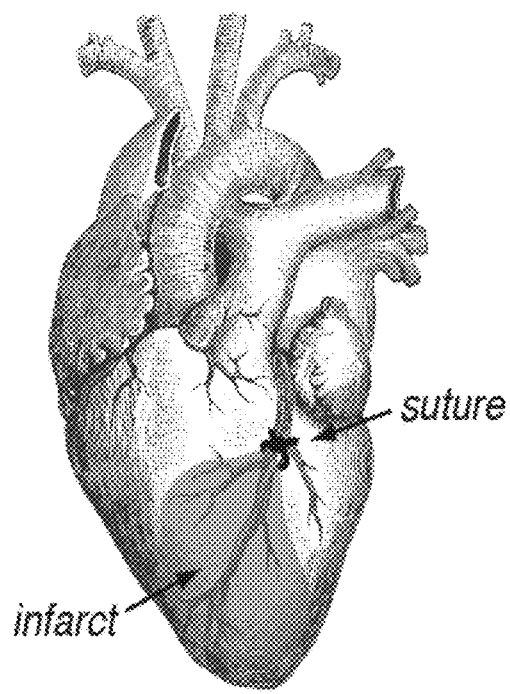
FIG. 3A shows according to an exemplary embodiment of the invention a schematic illustration of the induced myocardial infarction in heart of a rat model whereby the left anterior descending artery is sutured to prevent blood flow to the myocardium, leading to local myocardial infarction.
Figure 3B:
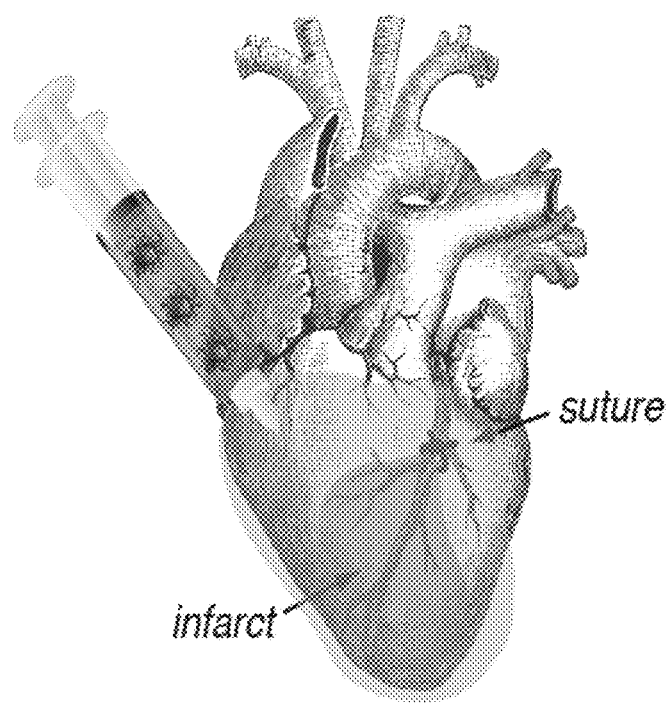
FIG. 3B. shows according to an exemplary embodiment of the invention a schematic illustration of application of anti-adhesion hydrogel including the shear-thinning and self-healing hydrogel according to the present invention and applied to the pericardial region of the heart.
Figure 4:
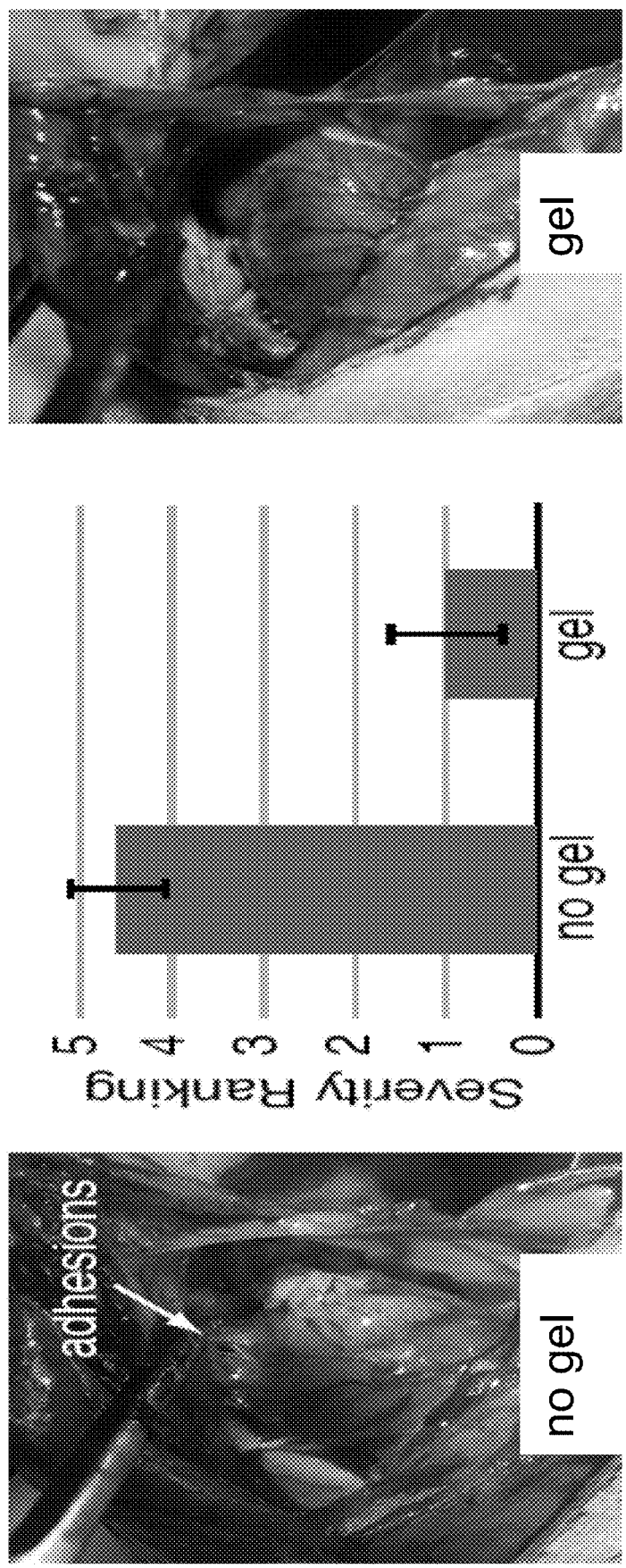
FIG. 4 shows according to an exemplary embodiment of the invention representative images of an untreated heart post-infarction with significant adhesions (left) and a treated heart post-infarction showing no adhesions (right). The bar chart showing the clinical severity ranking for adhesions in rats untreated and treated with the shear-thinning hydrogel according to the present invention.
Figure 5A:
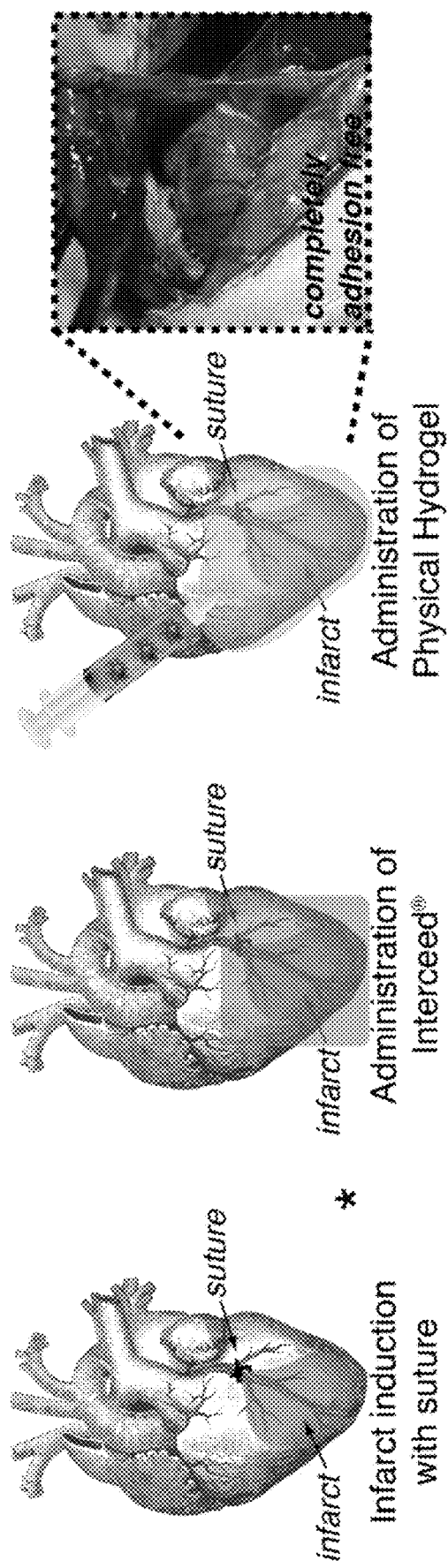
FIG. 5A shows according to an exemplary embodiment of the invention additional teachings and data compared to FIGS. 3A-B and FIG. 4.
Figure 5B:
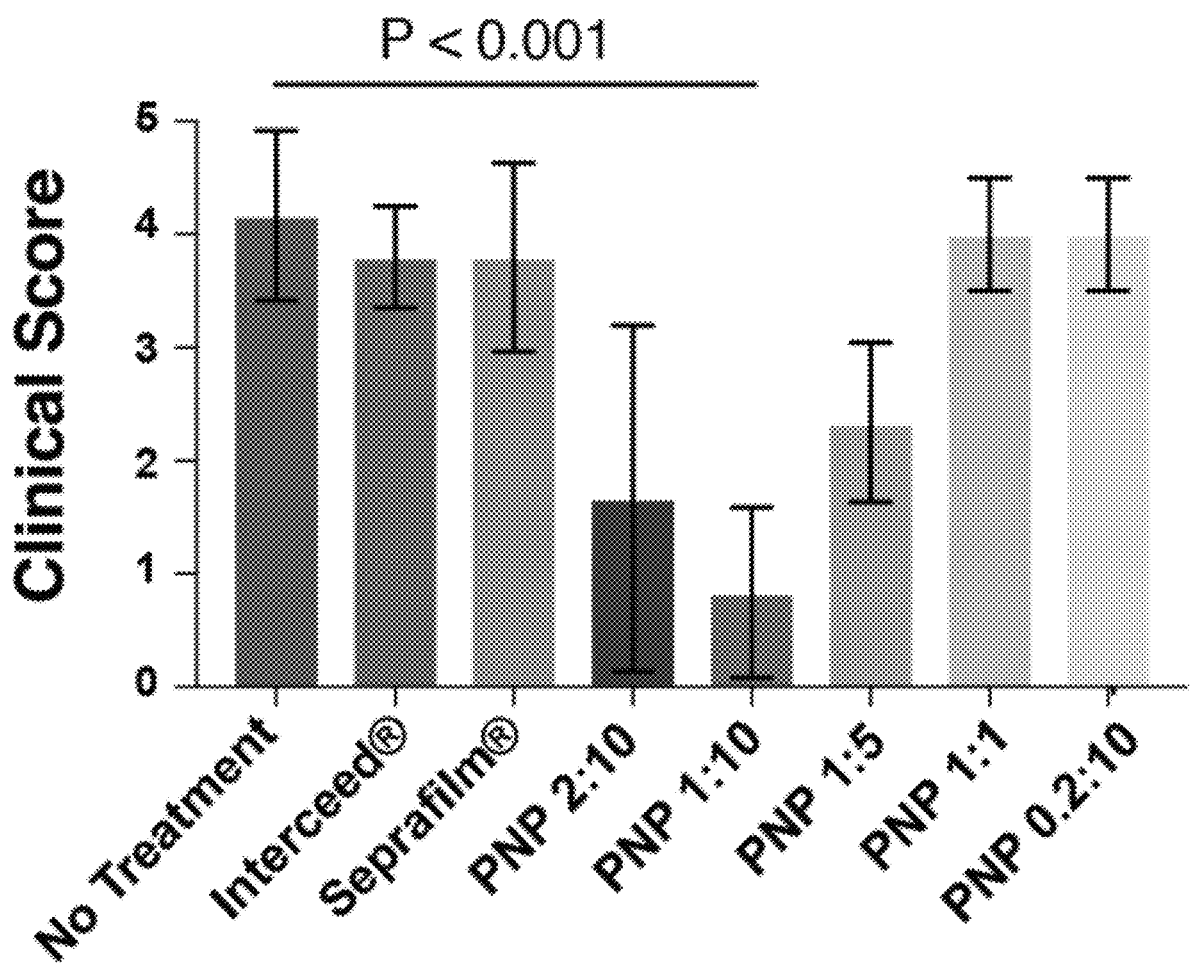
FIG. 5B shows double-blinded clinical scoring of adhesion formation one-month following induction of myocardial infarction demonstrates that application of PNP hydrogels dramatically reduces the incidence and severity of adhesions.
Figure 5C:
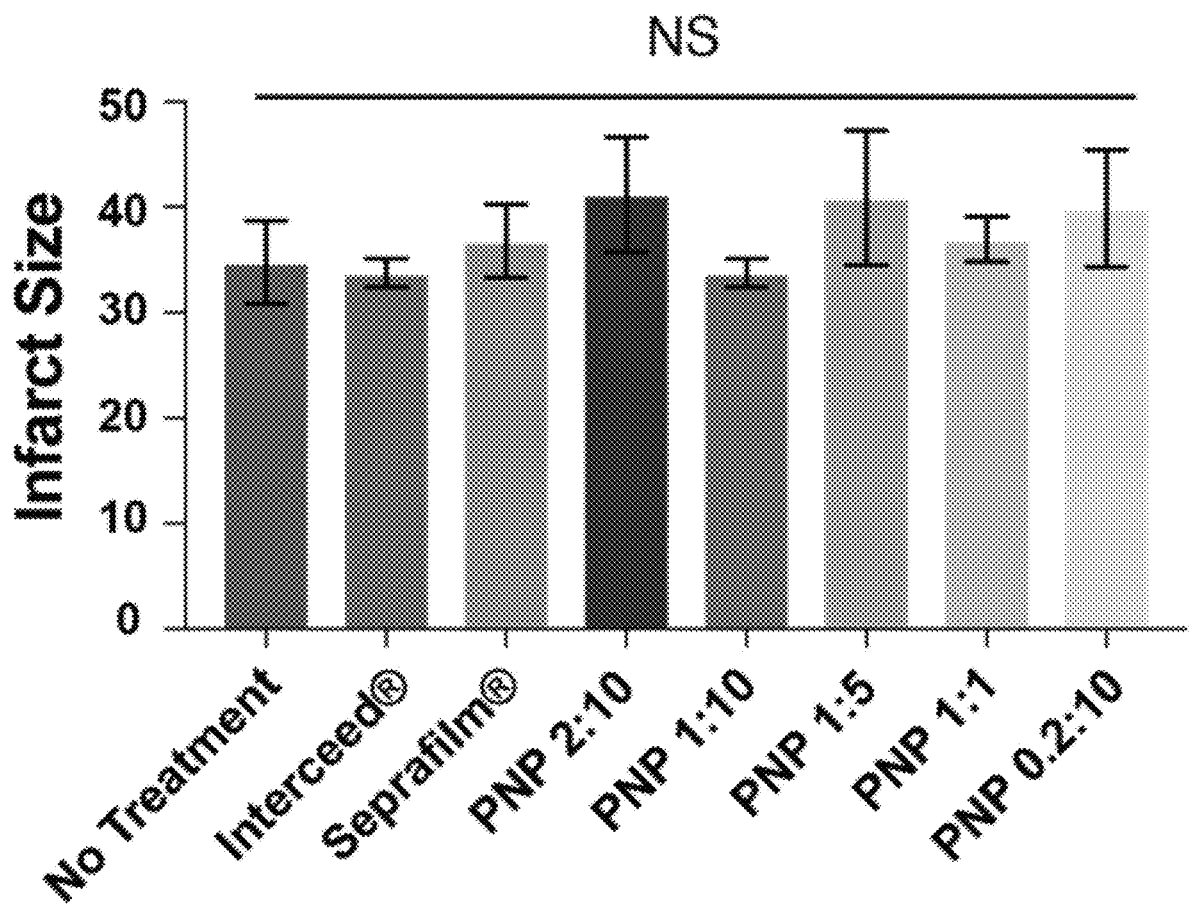
FIG. 5C shows infarct size was used to ensure consistency across groups. Data presented as mean±s.d. (n≥6). PNP formulation denoted as wt % HPMC-$C_{12}$: wt % PEG-PLA NPs (i.e., 1:10 refers to a formulation comprising HPMC-$C_{12}$ at 1 wt % and PEG-PLA NPs at 10 wt %).
Figure 6:
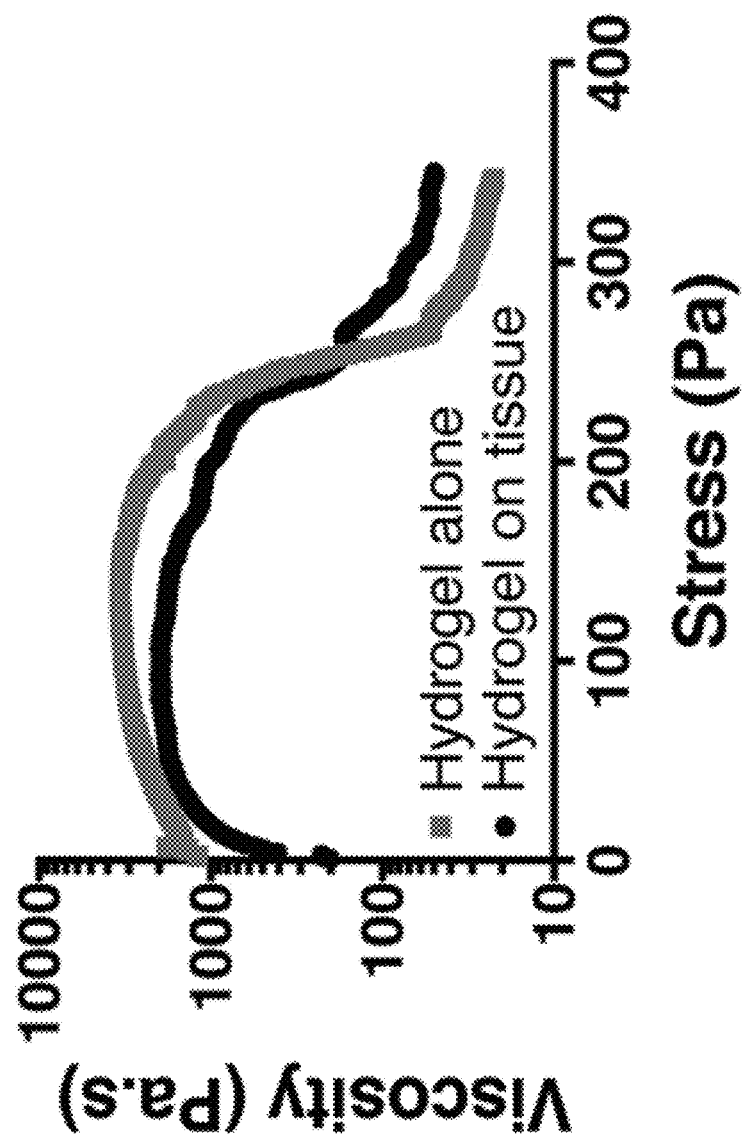
FIG. 6 shows according to an exemplary embodiment of the invention mechanical characterization of PNP hydrogel tissue adhesion. The adhesion of PNP hydrogels to tissue (rat hypodermis) is characterized using a yield stress measurement on a rheometer. In these experiments, we determined the yield behavior of PNP hydrogels alone in a standard geometry and when on rat hypodermis. The representative data shown for PNP 1:10 hydrogels shows that the yield stress is equivalent whether on tissue or not, indicating that yielding behavior is cohesive and therefore dictated by the gel mechanics.
Figure 6:
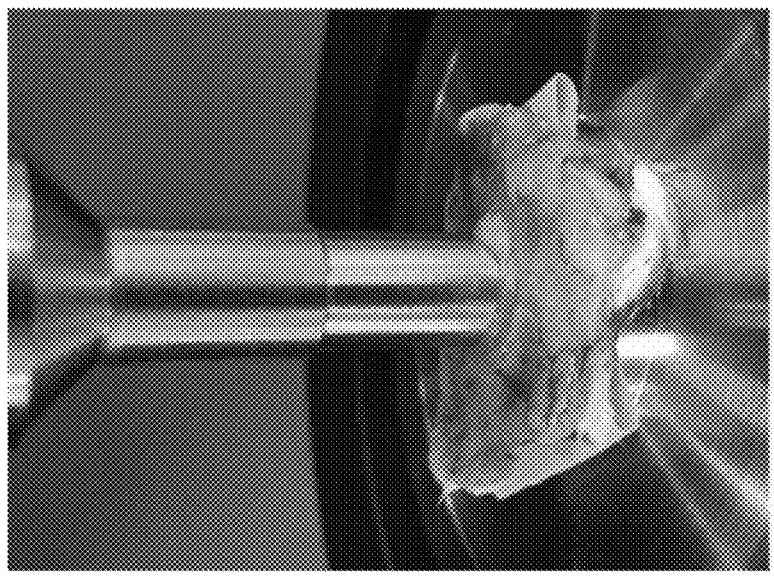
Figure 7:
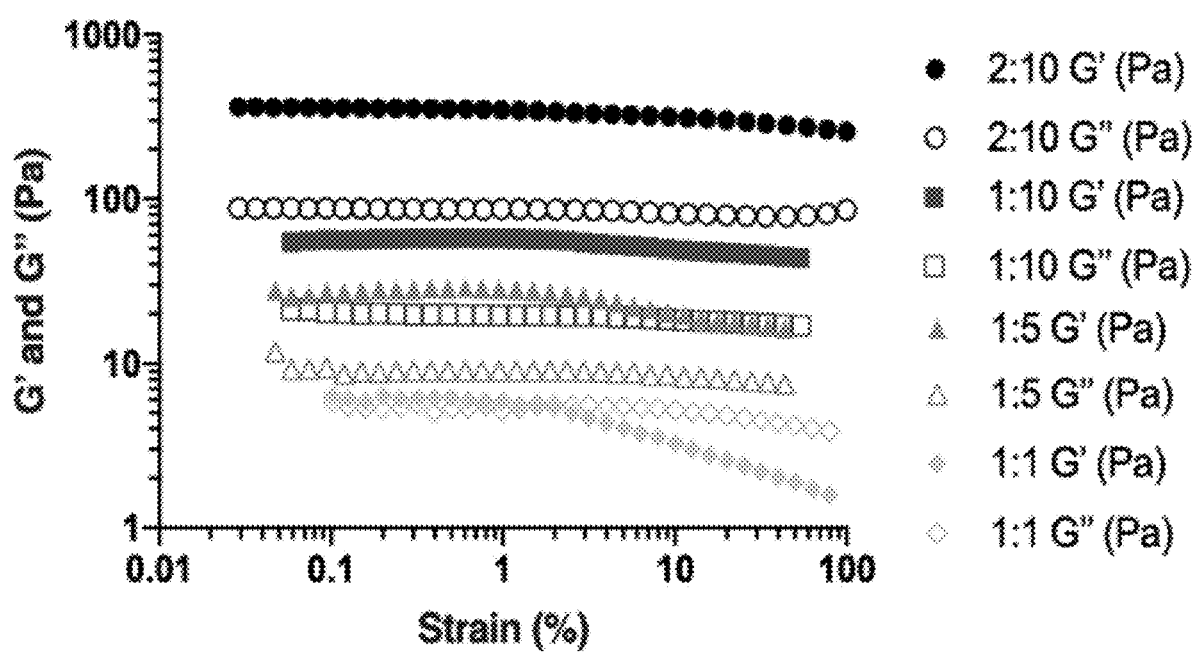
FIG. 7 shows according to an exemplary embodiment of the invention strain-dependent oscillatory shear rheology ($\omega$=10 rad s$^{-1}$, 25° C.).
Figure 8:
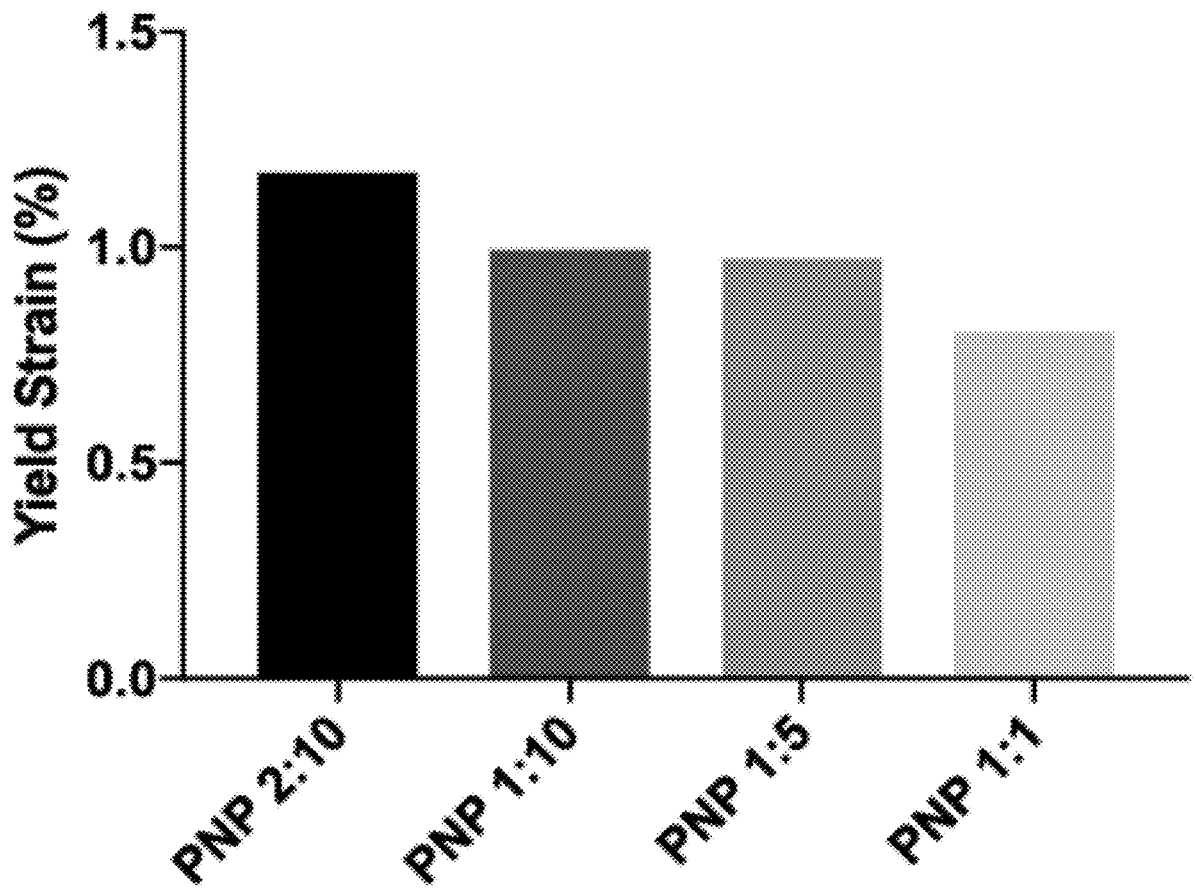
FIG. 8 shows according to an exemplary embodiment of the invention yield strain of PNP hydrogel formulations defined as the stain where the material deviates from the linear viscoelastic regime. Yield strain values are taken from the inflection point where tan $\delta$(G"/G') deviates from linearity.
Figure 9:
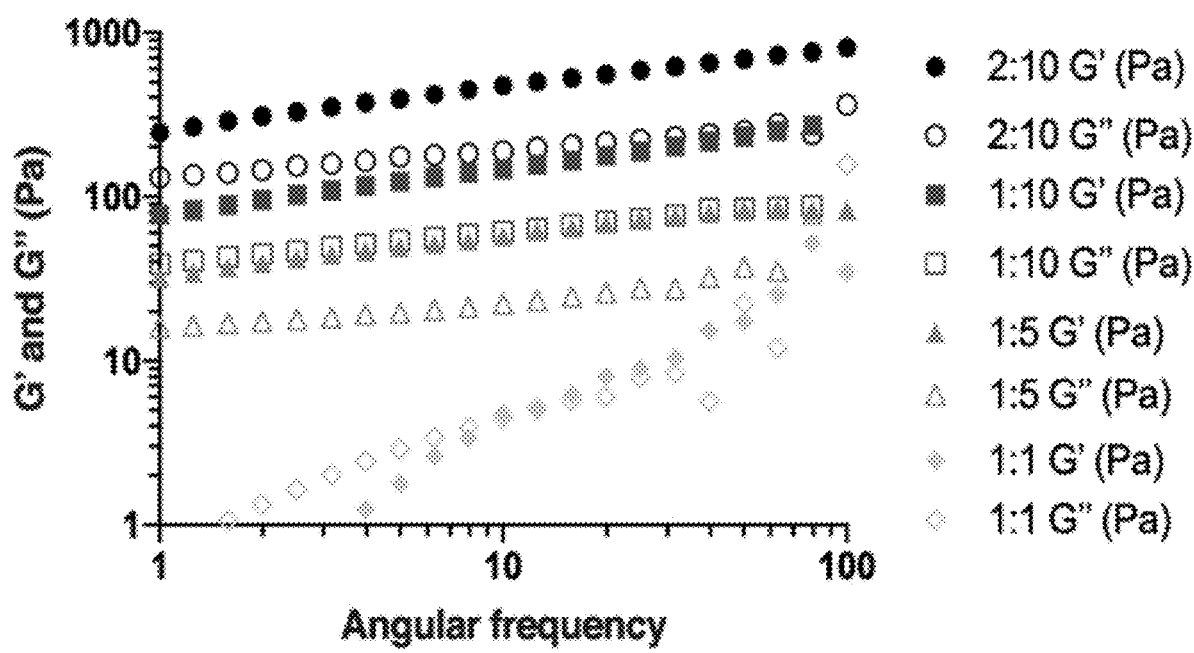
FIG. 9 shows according to an exemplary embodiment of the invention frequency-dependent oscillatory rheology of PNP hydrogels comprising HPMC-$C_{12}$ (x %) and PEG-PLA NPs (x %) (strain amplitude=2%, 25° C.).
Figure 10:
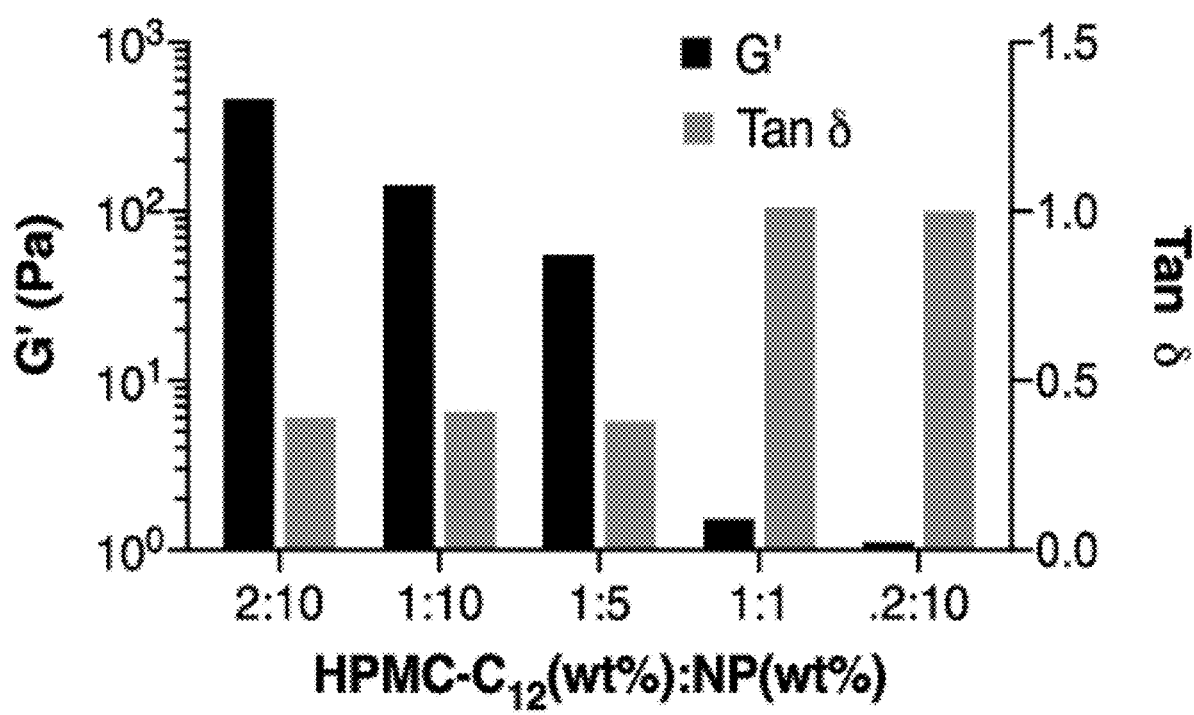
FIG. 10 shows according to an exemplary embodiment of the invention oscillatory rheological properties of hydrogels: storage modulus (G'; a measure of strength) and tan $\delta$(a measure of elasticity) values for different PNP hydrogel formulations.
Figure 11:
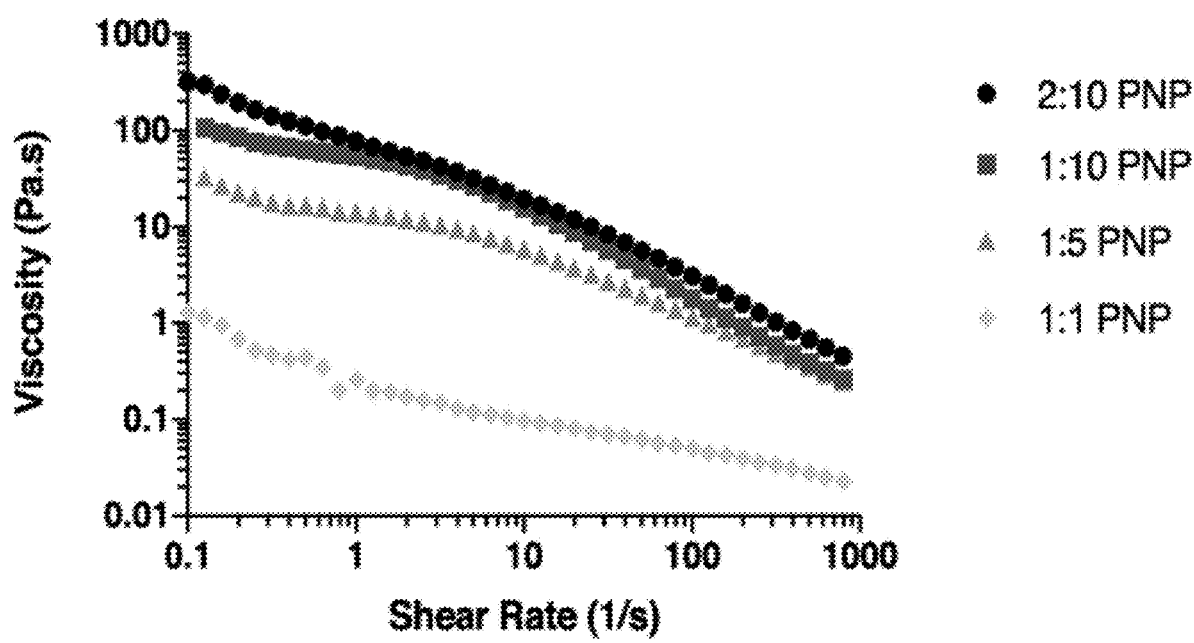
FIG. 11 shows according to an exemplary embodiment of the invention steady shear rheology of different PNP hydrogel formulations.
Figure 12:
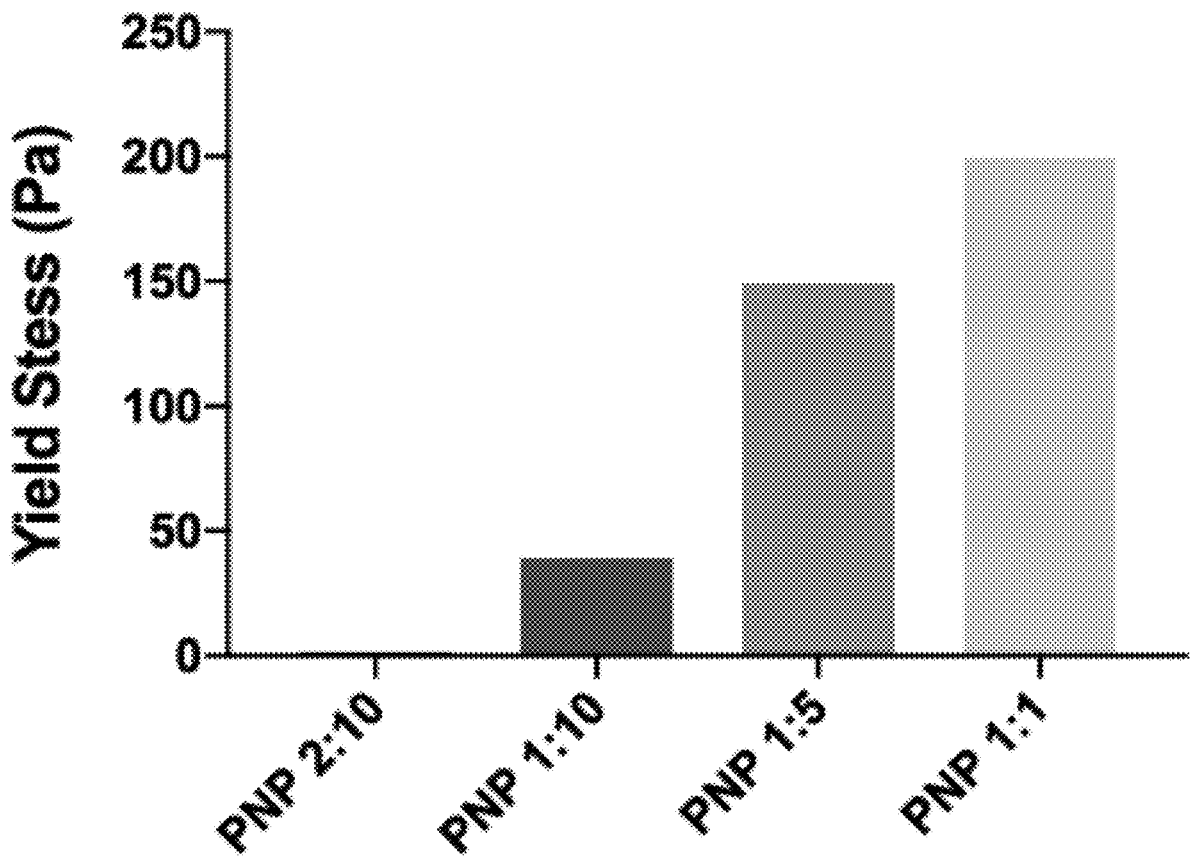
FIG. 12 shows according to an exemplary embodiment of the invention yield stress values of PNP hydrogel formulations obtained from the peak viscosity observed in a stress ramp performed at a rate of approximately 1.5 Pa/s.
Figure 13:
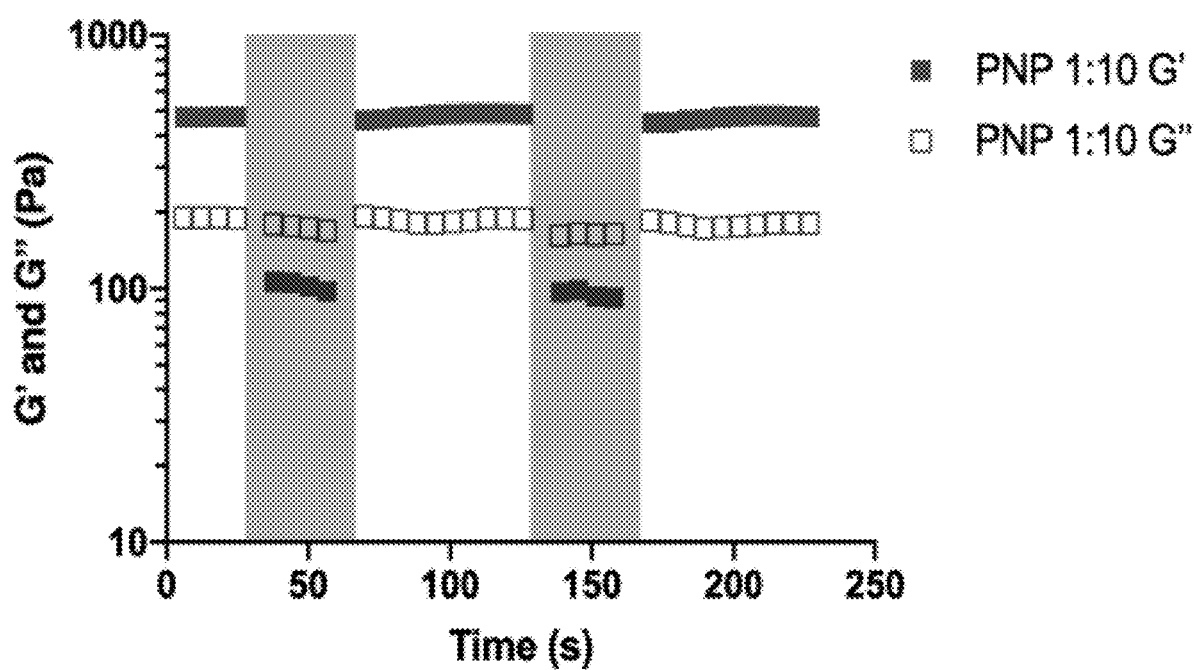
FIG. 13 shows according to an exemplary embodiment of the invention step-strain measurements of PNP hydrogels comprising HPMC-$C_{12}$ (1%) an PEG-PLA NPs (10%), whereby high stains (destructive; 750%) and low strains (0.5%) are alternated to assess the rate of self-healing, indicate that PNP gels completely recover their mechanical properties in less than 5s.

To demonstrate the utility of these materials to prevent adhesions, we used an established and highly reproducible model of myocardial infarction in rats where mature adhesions are formed in the thoracic cavity following a thoracotomy and myocardial infarction. In these studies, ten Sprague-Dawley rats experienced an induced myocardial infarction in which a thoracotomy is performed and the left anterior descending artery is permanently occluded with a suture producing an anterolateral myocardial infarction (FIG. 3A). The animals were randomized to receive pericardial delivery of 250 microLiter of PNP gel surrounding the heart (FIG. 3B) or no treatment for preventing adhesions. Following treatment, the thoracotomy is closed. Rats were sacrificed four weeks later to evaluate the anti-adhesive efficacy utilizing a standard adhesion scoring system on a scale from 0 to 5. The scores of adhesions were taken via a double-blinded process and are reported in FIG. 4. Qualitatively, there was a clearly visible difference in the number and severity of adhesions in the rats that were given treatment and the rats that were not (FIG. 4). In the control group, all rats presented with a score of 4 or 5 with an average score of 4.5, which demonstrates the successful establishment of a repeatable injury model in the thoracic cavity. Furthermore, a significantly lower adhesion score (P<0.001) was found in the PNP hydrogel treatment group (FIG. 4). In addition, not only were there minor to no adhesions in the treated group, but no PNP hydrogel residue remained in the thoracic cavity after the 4 week study, which supports the high efficacy of the anti-adhesion capabilities and biodegradation/resorbability of the PNP hydrogel system. These results have been reproduced in a sheep pericardial adhesion model whereby the heart is abraded to induce inflammation leading to mature adhesion formation (not shown). These two models are representative of the adhesion formation process that arises from any type of surgical procedure or bodily insult in any part of the body.

The biodegradable, shear-thinning and viscoelastic PNP hydrogel described supra represents a terrific example of this class of material and is easy and inexpensive to manufacture on scale, is exceedingly easy to use, and presents strong evidence in being highly effective in prevention of adhesions in a repeatable model for pericardial adhesions. The distinct functional attributes of the hydrogel uniquely allow for translational use in laparoscopic surgeries, which is impossible with most current treatments. We provide a distinct functional approach to anti-adhesion solutions in that our system is not a solid barrier and relies on complex viscoelastic behavior to maintain natural movement between tissues and organs.

Definition of PNP Hydrogel

The tissue adhesion prevention hydrogel is defined as a shear-thinning and viscoelastic supramolecular hydrogel that comprises cellulose derivatives and nanoparticles. The cellulose derivatives can be hydroxypropylmethylcellulose (HPMC), hydroxyethyl cellulose (HEC), hydroxypropylcellulose (HPC), ethylcellulose (EC), methylcellulose (MC), hydroxyethylmethylcellulose (HEMC), carboxymethylcellulose (CMC), carboxymethyl ethyl cellulose (CMEC) or derivatives of these compounds which have been modified with a saturated or unsaturated alkyl hydrophobic moiety (e.g., $C_{2-18}$, ethyl hexyl) or aryl hydrophobic moiety (e.g., phenyl, benzyl). The nanoparticles can be poly(ethyleneglycol)-block-poly(lactic acid) (PEG-PLA) nanoparticles, but is not limited to PEG-PLA as other nanoparticle compositions that are engineered to PNP hydrogels exhibiting the mechanical/physical properties as outlined infra.

Essential features of the barriers described above for maintaining separation between tissues and organs, thus preventing adhesion formation, are their shear-thinning, viscoelasticity, and rapid self-healing (FIGS. 7-13).

By viscoelastic, we mean the storage modulus (G') is dominant over the loss modulus (G") at some point as observed in an oscillatory frequency sweep measurement in the range of 0.1-100 rad/s on an oscillatory, rheometer performed in the linear viscoelastic regime, yet exhibiting complete stress relaxation following application of a constant strain of 500% within 15 minutes.

By shear-thinning, we mean the viscosity of the gel decreases with increasing shear rate in the range of 0.1-100 cycles/second as observed on an oscillatory rheometer.

By self-healing, we mean that either the modulus or the viscosity recovers at least 90% of its original value within 5 min in a step-strain (conducted with strains of 0.5% and 500%) or step-shear (conducted with shear rates of 0.1 cycles/second and 100 cycles/second) measurement, respectively, on an oscillatory rheometer.

Specifically, the physical characteristics of the PNP hydrogel which provide the adhesion prevention as desired and taught in this invention are:

A storage modulus (G') of 10-1000 Pa observed at a frequency of 10 rad/s and at a strain within the linear viscoelastic regime of the material using an oscillatory shear test in a parallel plate rheometer. In a preferred embodiment, the storage modulus (G') is about 100-200 Pa.

A yield stress of 1-1000 Pa observed using a stress ramp in a parallel plate rheometer, where about 100-200 is Pa preferred.

A linear viscoelasticity, defined as range of strains were tan delta (G"/G') is strain-independent, maintained at strains up to at least 0.5% observed in an oscillatory strain amplitude sweep observed at a frequency of 10 rad/s in a parallel plate rheometer, where about 1% is preferred.

A tan delta, defined as the ratio of the loss modulus over the storage modulus (G"/G'), less than 1 (where about 0.3-0.5 is preferred) when observed in an oscillatory shear test at a frequency of 10 rad/s and a strain within the linear viscoelastic regime of the material using a parallel plate rheometer Method of Making the PNP Hydrogel The PNP hydrogel are formed and engineered to ensure the essential physical characteristics, as outlined supra, for maintaining separation between tissues and organs, thus preventing adhesion formation, are their shear-thinning, viscoelasticity, and rapid self-healing. PNP hydrogels are formed by mixing aqueous solutions of HPMC-x (typically 3 wt %) and PEG-PLA NPs (typically 15 wt %) in a 1:2 ratio by volume such that the final composition the hydrogel is 1 wt % HPMC and 10 wt % PEG-PLA NPs. These gels formed rapidly upon mixing of the two components. The hydrogels may be applied to the tissue of interest following surgery by either spreading or spraying or injecting into any part of the body.

What is claimed is:

1. A method comprising:
   interposing a dynamically cross-linked supramolecular hydrogel between two animal tissue layers, the dynamically cross-linked supramolecular hydrogel comprising non-covalent interactions between nanoparticles and a hydrophobically modified cellulose derivative; and
   preventing formation of tissue adhesion between the two animal tissue layers with the interposed dynamically cross-linked supramolecular hydrogel.

2. The method of claim 1, wherein the cellulose derivative is hydroxypropylmethylcellulose (HPMC).

3. The method of claim 1, wherein the nanoparticles are poly(ethyleneglycol)-block-poly(lacticacid) (PEG-PLA) nanoparticles.

4. The method of claim 1, wherein the dynamically cross-linked supramolecular hydrogel is formed by combining a first aqueous solution that includes three percent weight by volume of the cellulose derivative and a second aqueous solution that includes fifteen percent weight by volume of the nanoparticles, the first and second aqueous solutions being combined in a 1:2 ratio by volume so that a final composition of the dynamically cross-linked supramolecular hydrogel is one percent weight by volume of the cellulose derivative and ten percent weight by volume of the nanoparticles.

5. The method of claim 1, wherein the dynamically cross-linked supramolecular hydrogel is shear-thinning.

6. The method of claim 1, wherein the dynamically cross-linked supramolecular hydrogel is self-healing.

7. The method of claim 1, wherein the dynamically cross-linked supramolecular hydrogel includes polymer chains and non-covalent cross-linking bonds between at least some of the polymer chains.

8. The method of claim 7, wherein the dynamically cross-linked supramolecular hydrogel is shear-thinning and the shear-thinning of the dynamically cross-linked supramolecular hydrogel is achieved via dissociation of at least some of the non-covalent cross-linking bonds between the non-covalently cross-linked polymer chains.

9. The method of claim 7, wherein the dynamically cross-linked supramolecular hydrogel is self-healing and the self-healing of the dynamically cross-linked supramolecular hydrogel is achieved via reestablishment of the non-covalent cross-linking bonds between at least some of the non-covalently cross-linked polymer chains.

10. The method of claim 1, wherein the dynamically cross-linked supramolecular hydrogel further comprises tissue adhesive polymers that act to adhere the dynamically cross-linked supramolecular hydrogel to the two animal tissue layers.

11. The method of claim 1, wherein the two animal tissue layers are internal to a body of an animal.

12. The method of claim 1, wherein the interposing comprises spraying the dynamically cross-linked supramolecular hydrogel between the two animal tissue layers.

13. The method of claim 1, wherein the interposing comprises injecting the dynamically cross-linked supramolecular hydrogel between the two animal tissue layers.

14. A method comprising:
interposing a dynamically cross-linked supramolecular hydrogel between two animal tissue layers to prevent formation of tissue adhesion between the two animal tissue layers, the dynamically cross-linked supramolecular hydrogel being from one to two percent weight by volume hydrophobically modified cellulose derivative, and from five to ten percent weight by volume nanoparticles, wherein the nanoparticles non-covalently interact with the hydrophobically modified cellulose derivative.

15. The method of claim 14, wherein the dynamically cross-linked supramolecular hydrogel includes polymer chains and non-covalent cross-linking bonds between at least some of the polymer chains.

16. The method of claim 15, wherein the dynamically cross-linked supramolecular hydrogel is shear-thinning and the shear-thinning of the dynamically cross-linked supramolecular hydrogel is achieved via dissociation of at least some of the non-covalent cross-linking bonds between the non-covalently cross-linked polymer chains.

17. The method of claim 15, wherein the dynamically cross-linked supramolecular hydrogel is self-healing and the self-healing of the dynamically cross-linked supramolecular hydrogel is achieved via reestablishment of the non-covalent cross-linking bonds between at least some of the non-covalently cross-linked polymer chains.

18. The method of claim 14, wherein the interposing comprises spraying the dynamically cross-linked supramolecular hydrogel between the two animal tissue layers.

19. The method of claim 14, wherein the interposing comprises injecting the dynamically cross-linked supramolecular hydrogel between the two animal tissue layers.

20. The method of claim 1, wherein the hydrophobically modified cellulose derivative is a cellulose derivative modified with a hydrophobic saturated or unsaturated alkyl moiety, or with a hydrophobic aryl moiety.

21. The method of claim 14, wherein the hydrophobically modified cellulose derivative is a cellulose derivative modified with a hydrophobic saturated or unsaturated alkyl moiety, or with a hydrophobic aryl moiety.

* * * * *